(12) United States Patent
Kato et al.

(10) Patent No.: US 11,261,395 B2
(45) Date of Patent: Mar. 1, 2022

(54) FULLERENE COMPOUND, LUBRICANT FOR MAGNETIC RECORDING MEDIUM, AND MAGNETIC RECORDING MEDIUM

(71) Applicant: SHOWA DENKO K.K., Tokyo (JP)

(72) Inventors: Tsuyoshi Kato, Ichihara (JP); Kentaro Watanabe, Chiba (JP); Yasuyuki Ueda, Yokohama (JP)

(73) Assignee: SHOWA DENKO K.K., Tokyo (JP)

( * ) Notice: Subject to any disclaimer, the term of this patent is extended or adjusted under 35 U.S.C. 154(b) by 0 days.

(21) Appl. No.: 16/972,813

(22) PCT Filed: Jun. 10, 2019

(86) PCT No.: PCT/JP2019/022850
§ 371 (c)(1),
(2) Date: Dec. 7, 2020

(87) PCT Pub. No.: WO2019/240058
PCT Pub. Date: Dec. 19, 2019

(65) Prior Publication Data
US 2021/0253968 A1    Aug. 19, 2021

(30) Foreign Application Priority Data
Jun. 12, 2018   (JP) .............................. JP2018-111894

(51) Int. Cl.
*C10M 103/02* (2006.01)
*C10M 105/72* (2006.01)
(Continued)

(52) U.S. Cl.
CPC ........... *C10M 105/72* (2013.01); *C07C 57/50* (2013.01); *C07C 65/30* (2013.01); *C07C 225/06* (2013.01);
(Continued)

(58) Field of Classification Search
CPC .............. C10M 105/72; C10M 103/02; C10M 2213/06; C10M 2215/04; C10M 2201/041;
(Continued)

(56) References Cited

U.S. PATENT DOCUMENTS

2015/0162044 A1   6/2015   Hanawa et al.
2016/0347703 A1   12/2016   Igarashi et al.

FOREIGN PATENT DOCUMENTS

EP    3 318 553 A1    5/2018
JP    05-093059 A     4/1993
(Continued)

OTHER PUBLICATIONS

International Search Report of PCT/JP2019/022850 dated Aug. 27, 2019 [PCT/ISA/210].

*Primary Examiner* — Taiwo Oladapo
(74) *Attorney, Agent, or Firm* — Sughrue Mion, PLLC

(57) ABSTRACT

The invention provides a fullerene compound; a lubricant that is for a magnetic recording medium and that contains the fullerene compound; and a magnetic recording medium. The fullerene compound is an ionic liquid that is represented by general formula (1) and is formed from a Bronsted acid ($H_{n1}X$) and a Bronsted base ($[R_2R_3)N-]_{m1}-R_1$); wherein one of the Brønsted acid and the Broønsted base contains a group having a fullerene; and the other contains a perfluoroalkyl chain.

(Continued)

[Formula 1]

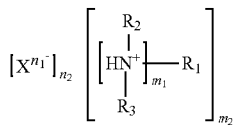

(1)

10 Claims, 1 Drawing Sheet

(51) Int. Cl.
*G11B 5/725* (2006.01)
*C07C 57/50* (2006.01)
*C07C 65/30* (2006.01)
*C07C 225/06* (2006.01)
*C07C 305/22* (2006.01)
*C07D 487/22* (2006.01)
*C10M 105/60* (2006.01)
*C10M 105/70* (2006.01)
*C10N 20/00* (2006.01)
*C10N 40/18* (2006.01)

(52) U.S. Cl.
CPC .......... *C07C 305/22* (2013.01); *C07D 487/22* (2013.01); *C10M 105/60* (2013.01); *C10M 105/70* (2013.01); *G11B 5/7253* (2020.08); *C07C 2601/16* (2017.05); *C07C 2604/00* (2017.05); *C10M 2201/0413* (2013.01); *C10M 2215/265* (2013.01); *C10M 2215/305* (2013.01); *C10M 2219/044* (2013.01); *C10N 2020/077* (2020.05); *C10N 2040/18* (2013.01)

(58) Field of Classification Search
CPC .............. C10M 105/60; C10M 105/70; C10M 2215/265; C10M 2215/305; C10M 2219/044; G11B 5/7253; C07C 57/50; C07C 65/30; C07C 225/06; C07C 305/22; C07C 2604/00; C07C 2601/16; C10N 2030/08; C10N 2020/06; C10N 2040/14; C10N 2030/06; C10N 2050/025; C10N 2020/04; C10N 2020/077; C10N 2040/18; C07D 303/48; C07D 487/22
See application file for complete search history.

(56) References Cited

FOREIGN PATENT DOCUMENTS

| JP | 2005-336309 A | 12/2005 | |
|---|---|---|---|
| JP | 2015-109129 A | 6/2015 | |
| JP | 2015-135710 A | 7/2015 | |
| JP | 2016-009509 A | 1/2016 | |
| JP | 2017-014192 A | 1/2017 | |
| WO | 2015/125940 A1 | 8/2015 | |
| WO | WO-2017006812 A1 * | 1/2017 | .......... C10M 105/54 |

* cited by examiner

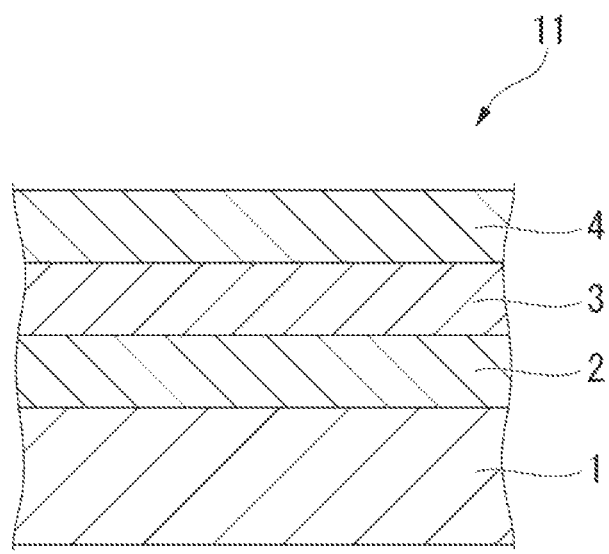

FULLERENE COMPOUND, LUBRICANT FOR MAGNETIC RECORDING MEDIUM, AND MAGNETIC RECORDING MEDIUM

TECHNICAL FIELD

Cross Reference To Related Applications

This application is a National Stage of International Application No. PCT/JP2019/022850 filed on Jun. 10, 2019, claiming priority based on Japanese Patent Application No. 2018-111894 filed in Japan on Jun. 12, 2018, the contents of which are incorporated herein by reference.

The present invention relates to a fullerene compound, a lubricant for a magnetic recording medium, and a magnetic recording medium.

BACKGROUND OF THE INVENTION

Recently, as a method for improving the recording capacity of a magnetic recording medium, HAMR (Heat Assisted Magnetic Recording) has been developed. This HAMR system is a next-generation recording technology that records and reproduces magnetic fields while applying thermal offset by way of local heating with near-field light. By using this technology, even a weak signal is not affected by surrounding thermal noise, and reliability can be maintained. However, since the HAMR system is heated by near-field light, further heat resistance and repeated durability are required for the lubricant. Specifically, heat resistance of 250° C. or more is required. Further, even under such an environment, in order to realize high reliability of the magnetic recording medium device, it is important to design a lubricant film capable of maintaining excellent lubricating property even if the magnetic recording medium device slides repeatedly.

In response to this demand, there are patents proposing the use of materials with excellent heat resistance and the use of ionic liquids.

For example, Patent Document 1 discloses a compound of a perfluoropolyether having a carboxyl group at the terminal, and a diamine. Excellent lubricating property and durability are disclosed.

Patent Document 2 discloses a lubricant containing an ionic liquid formed from a sulfonic acid or a carboxylic acid having a perfluoropolyether skeleton, and an amine basing a perfluoroalkyl chain bonded to a nitrogen atom via an unsubstituted alkylene group having 2 to 5 carbon atoms. Excellent heat resistance and lubricating property (low coefficient, of friction) are disclosed.

Patent Document 3 discloses a lubricant containing a fullerene derivative having a fullerene skeleton and a perfluoropolyether chain. An excellent coaling property is disclosed.

However, these prior arts do not provide sufficient heat resistance and lubricating property in the next-generation recording technology such as the HAMR system.

Patent Document

Patent Document 1: Japanese Unexamined Patent Application Publication No. H5-93059
Patent Document 2: Japanese Unexamined Patent Application Publication No. 2016-9509
Patent Document 3: Japanese Unexamined Patent Application Publication No. 2015-135710

SUMMARY OP THE INVENTION

Problem to Be Solved by the Invention

It is an object of the present invention to provide a fullerene compound which can be suitably used as a material of a lubricant for a magnetic recording medium which can realize sufficient heat resistance and lubricating property even in a next-generation recording technology such as the HAMR system. It is another object of the present invention to provide a magnetic recording medium having a lubricant for a magnetic recording medium containing die fullerene compound of die present invention.

Means to Solve the Problem

As a result of intensive investigation, the present inventors found that an ionic liquid compound formed from a Bronsted acid and a Bronsted base, one of which contains a group having a fullerene is a promising compound.

In other words, the present invention relates to the following:

[1] A fullerene compound, which is an ionic liquid represented by general formula (1), wherein the ionic liquid is formed from a Bronsted acid ($H_{n1}X$) and a Bronsted base ($[R_2R_3)N\text{—}]_{m1}\text{—}R_1$);
one of the Bronsted acid and the Bronsted base comprises a group having a fullerene; and
the other one of the Bronsted acid and the Bronzed base comprises a perfluoroalkyl chain.

[Formula 1]

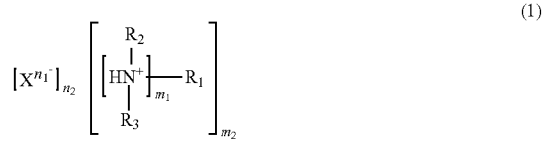

(1)

wherein at least one of $R_1$, $R_2$ and $R_3$ is a hydrocarbon group having 1 to 20 carbon atoms;
at least one of X, $R_1$, $R_2$ and $R_3$ has a fullerene skeleton, and at least one of X, $R_1$, $R_2$ and $R_3$ has a perfluoroalkyl chain;
$R_2$ and $R_3$ may be bonded to each other to form a nitrogen-containing heterocycle; and
$n_1$, $n_2$, $m_1$, and $m_2$ are integers of 1 to 6, and $n_1 \times n_2 = m_1 \times m_2$.

[2] The fullerene compound according to [1], wherein the Bronsted acid, in a molecule, comprises
a fullerene skeleton, and
a sulfonic acid group or a carboxylic acid group; and
the Bronsted base comprises a perfluoropolyether chain.

[3] The fullerene compound according to [1], wherein the Bronsted acid, in a molecule, comprises
a perfluoropolyether chain, and
a sulfonic acid group or a carboxylic acid group; and
the Bronsted base comprises a fullerene skeleton.

[4] The fullerene compound according to [1] or [2], wherein the Bronsted acid is a compound represented by formula (6), (7), or (8);
the Bronsted base is a compound represented by formula (10) or (11),

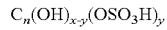

(6)

wherein $C_n$ represents a fullerene which is a base structure of polyhydroxylated fullerene hydrogen sulfate ester;

x is a number in the range of 10 to 30:

y is a number in the range of 5 to 10; and $C_n$ is at least one kind selected from $C_{60}$, $C_{70}$, $C_{76}$, $C_{78}$, $C_{80}$, $C_{82}$, and $C_{84}$.

[Formula 2]

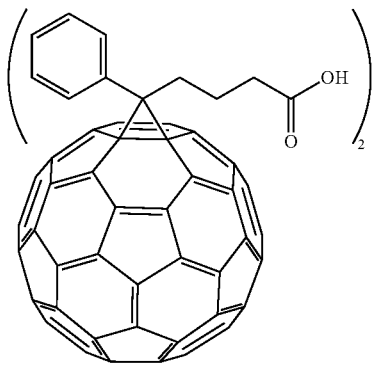

(7)

[Formula 3]

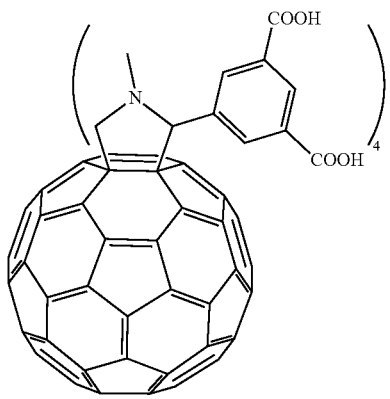

(8)

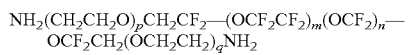

(10)

wherein p and q are 1 to 3; m is 1 to 30; and n is 0 to 30.

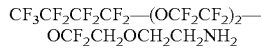

(11)

[5] The fullerene compound according to [1] or [3], wherein the Bronsted acid is a compound represented by any one of the following formulae (12) to (15); and the Bronsted base is a compound represented by formula (16),

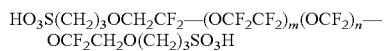

(12)

wherein m is 1 to 30 and n is 0 to 30.

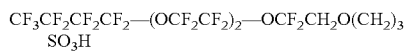

(13)

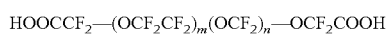

(14)

wherein m is 1 to 30 and n is 0 to 30,

(15)

[Formula 4]

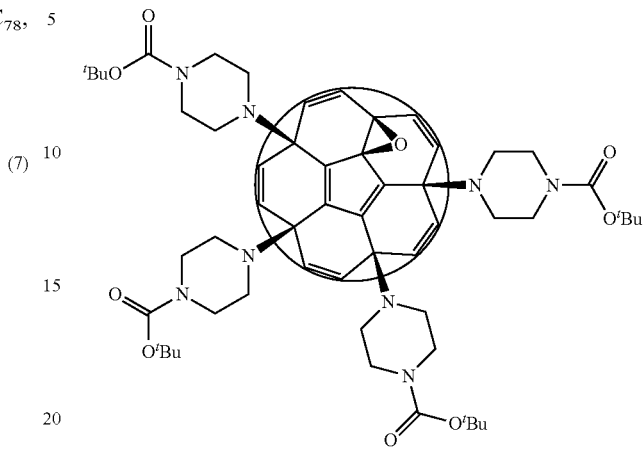

(16)

[6] The fullerene compound according to any one of [1] to [5], wherein the thermal decomposition temperature of the ionic liquid is 300° C. or higher.

[7] The fullerene compound according to any one of [1] to [6], wherein the number average molecular weight is in the range of 500 to 20,000.

[8] A lubricant for a magnetic recording medium comprising the fullerene compound according to any one of [1] to [7].

[9] A magnetic recording medium in which at least a magnetic layer, a protective layer, and a lubricant layer are sequentially provided on a substrate, wherein the lubricant layer contains the fullerene compound according to any one of [1] to [7].

[10] The magnetic recording medium according to [9], wherein the lubricant layer has an average film thickness of 0.5 nm to 2.5 nm.

Effect of the Invention

According to the present invention, thermal stability such as evaporation or thermal decomposition of the lubricant can be improved, and excellent lubrication characteristics can be maintained over a long period of time. By using this lubricant as a magnetic recording medium, it is possible to provide a magnetic recording medium having high reliability, particularly a magnetic recording medium having high reliability even in the HAMR system.

DESCRIPTION OF THE DRAWING

FIG. 1 is a cross-sectional view showing an example of a hard disk according to an embodiment of the present invention.

DETAILED DESCRIPTION OF THE INVENTION

Embodiments of the present invention will now be described in detail.

The compound of the present invention is represented by general formula (1). The compound is tut ionic liquid formed from a Bronsted acid ($H_{n1}X$) and a Bronsted base ($[(R_2R_3)N-]_{m1}-R_1$). One of the Bronsted acid and the Bronsted base contains a group having a fullerene and the other one of the Bronsted acid and the Bronsted base contains a perfluoroalkyl chain.

[Formula 5]

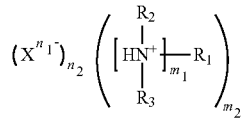
(1)

In general formula (1), at least one of $R_1$, $R_2$, and $R_3$ is a hydrocarbon group having 1 to 20 carbon atoms; at least one of X, $R_1$, $R_2$, and $R_3$ has a fullerene skeleton; and at least one of X, $R_1$, $R_2$, and $R_3$ has a perfluoroalkyl chain. $R_2$ and $R_3$ may be bonded to each other to form a nitrogen-containing heterocycle. $n_1$, $n_2$, $m_1$, and $m_2$ are integers of 1 to 6 and $n_1 \times n_2 = m_1 \times m_2$.

Examples of the hydrocarbon group having 1 to 20 carbon atoms of the present invention include an alkyl group having 1 to 20 carbon atoms, an alkenyl group having 1 to 20 carbon atoms, an aryl group having 1 to 20 carbon atoms, and an aralkyl group having 1 to 20 carbon atoms. $R_2$ and $R_1$ may be bonded to each other to form a nitrogen-containing heterocycle.

When $m_1$ is an integer of 2 to 6, then $R_1$ is a hydrocarbon group with $m_1$ bonding sites. The hydrocarbon group preferably has a fullerene skeleton or a perfluoroalkyl chain. $R_2$ and $R_3$ are each preferably independently a hydrogen atom or a hydrocarbon group having 1 to 20 carbon atoms. The hydrocarbon group having 1 to 20 carbon atoms may have a substituent.

[Fullerene Skeleton]

The fullerene skeleton of the present invention includes fullerenes having 60 to 120 carbon atoms, dimers or trimers thereof, and the like. More specifically, there are $C_{60}$, $C_{70}$, $C_{76}$, $C_{78}$, $C_{82}$, $C_{84}$, $C_{90}$, $C_{94}$, and $C_{96}$. Of these, $C_{60}$ and $C_{70}$ are preferable from the viewpoint of solubility.

[Perfluoroalkyl Chain]

The perfluoroalkyl chain of the present invention is preferably a perfluoroalkyl chain having 1 to 30 carbon atoms.

The perfluoroalkyl chain of the present invention may have an ether bond between the two ends of the chain. Examples include perfluoromethylene oxide polymers, perfluoroethylene oxide polymers, perfluoro-n-propylene oxide polymers, and perfluoroethylene oxide polymers: and copolymers thereof. The molecular weight of the perfluoroalkyl is not particularly limited, but is preferably 500 to 10,000 and particularly preferably 1,000 to 5,000.

As the perfluoroalkyl chain of the present invention, the following structures are preferably used.

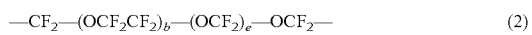 (2)

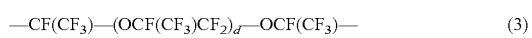 (3)

 (4)

 (5)

In the formulae (2), (3), and (4), b, d, and e each represent an integer of 1 to 30, and c represents an integer of 0 to 30.

The number average molecular weight (Mn) of the fluorine-containing ether compound is a value measured by $^1$H-NMR and $^{19}$F-NMR of AVANCE III 400 manufactured by Barker Biospin Co., Ltd. Specifically, the number of repeating units of the PEPE chain was calculated from the integral value measured by $^{19}$F-NMR, and the number average molecular weight was calculated.

As the NMR solvent, a single or mixed solvent of d-acetone, d-tetrahydrofuran, d-toluene, and hexafluorobenzene was used.

[Ionic Liquid]

The ionic liquid is formed from, for example, a carboxylic acid having a fullerene skeleton and an amine having a perfluoroalkyl chain, a sulfonic acid having a fullerene skeleton and an amine having a perfluoroalkyl chain, a carboxylic acid having n perfluoroalkyl chain and an amine having a fullerene skeleton, or a sulfonic acid having a perfluoroalkyl chain and an amine having a fullerene skeleton. Among them, a combination of a carboxylic acid having a fullerene skeleton and an amine having a perfluoroalkyl chain is preferable in view of ease of synthesis.

In order to obtain sufficient lubricating property, it is desirable that there are two or more perfluoroalkyl chains per fullerene molecule. For example, an ionic liquid formed from a group having a fullerene skeleton to which two or more carboxylic acids ate bonded and an amine having a perfluoroalkyl chain is desirable. When two or more perfluoroalkyl chains are used, lubricity and heat resistance can both be achieved.

The number average molecular weight of the fullerene compound of the present invention is preferably within the range of 500 to 10,000, and more preferably within the range of 1,000 to 5,000.

First Embodiment

[Fullerene Compound]

The fullerene compound of the first embodiment is an tonic liquid represented by general formula (1), wherein the ionic liquid is formed from Bronsted acid ($H_{n1}X$) and Bronsted base ($[R_2R_3)N-]_{m1}-R_1$); the Bronsted acid ($H_{n1}X$) contains a group having a fullerene; and the Bronsted base ($[R_2R_3)N-]_{m1}-R_1$) contains a perfluoroalkyl chain.

[Formula 6]

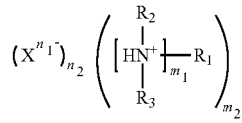
(1)

In general formula (1), at least one of $R_1$, $R_2$, and $R_3$ is a hydrocarbon group having 1 to 20 carbon atoms; X has a fullerene skeleton; and at least one of $R_1$, $R_2$, and $R_3$ has a perfluoroalkyl chain. $R_2$ and $R_3$ may be bonded to each other to form a nitrogen-containing heterocycle; $n_1$, $n_2$, $m_1$, and $m_2$ are integers of 1 to 6; and $n_1 \times n_2 = m_1 \times m_2$.

The fullerene skeleton is preferably $C_{60}$ or $C_{70}$.

Preferably, $n_1$ is an integer of 2 to 6 and $n_2$ is 1. More preferably, $n_1$ is an integer of 2 to 4 and $n_2$ is 1. When $n_1$ is 2 or more, lubricating property and heat resistance can both be achieved.

Preferably, $m_1$ is 1 or 2, $m_2$ is 1 to 6, and $n_1 \times n_2 = m_1 \times m_2$. More preferably, $m_1$ is 1 or 2, $m_2$ is 1 to 4, and $n_1 \times n_2 = m_1 \times m_2$.

When $m_1$ is an integer of 2 to 6, $R_1$ is a hydrocarbon group having 1 to 20 carbon atoms with $m_1$ bonding sites. The hydrocarbon group having 1 to 20 carbon atoms preferably has a perfluoroalkyl chain. $R_2$ and $R_3$ are each preferably independently a hydrogen atom or a hydrocarbon group having 1 to 20 carbon atoms. $R_2$ and $R_3$ are more preferably hydrogen atoms.

[Bronsted Acid]

The Bronsted acid according to the present embodiment includes u sulfonic acid having a fullerene skeleton, a carboxylic acid having a fullerene skeleton, and the like.

The sulfonic acid having the fullerene skeleton can be synthesized from fullerene and fuming sulfuric acid, for example, by the method described in JP 2005-8564 A1.

The specific structure is, for example, Compound 6 represented by the following formula (6).

In the formula, $C_n$ represents a fullerene which is a base structure of polyhydroxylated fullerene hydrogen sulfate ester, x is a number in the range of 10 to 30, and y is a number in the range of 5 to 10. $C_n$ is at least one kind selected from $C_{60}$, $C_{70}$, $C_{76}$, $C_{78}$, $C_{80}$, $C_{82}$, $C_{84}$, and the like.

Compound 6 represented by the above formula (6) is preferably Compound 6A represented by the following formula (6A).

[Formula 7]

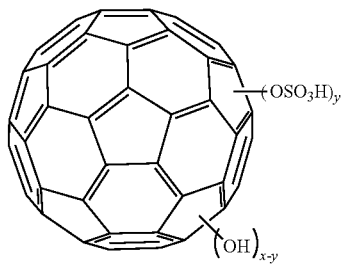

(6A)

In the formula, x is a number in the range of 10 to 30 and y is a number in the range of 5 to 10. Preferably, x is 10 and y is 5.

As the carboxylate acid having the fullerene skeleton, for example, a hydrolysate of phenyl $C_{61}$ butyricacid methyl ester, a hydrolysate of bis-phenyl $C_{61}$ butyricacid methyl ester (Compound 7 represented by formula (7)), a hydrolysate of phenyl $C_{71}$ butyricacid methyl ester, or the like can ho suitably used. A hydrolysate (Compound 8 represented by formula (8)) of a compound obtained by reacting fullerene with N-methylglycine and an aldehyde (Compound 9 represented by formula (9)) can also he suitably used.

[Formula 8]

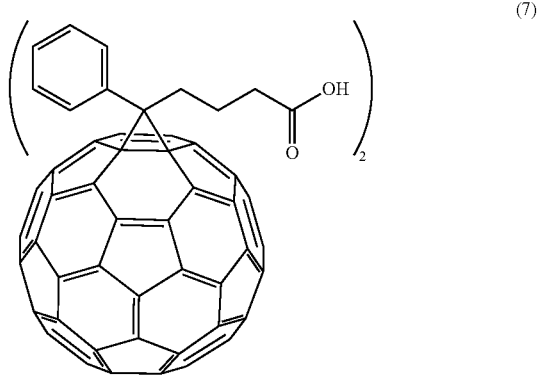

(7)

[Formula 9]

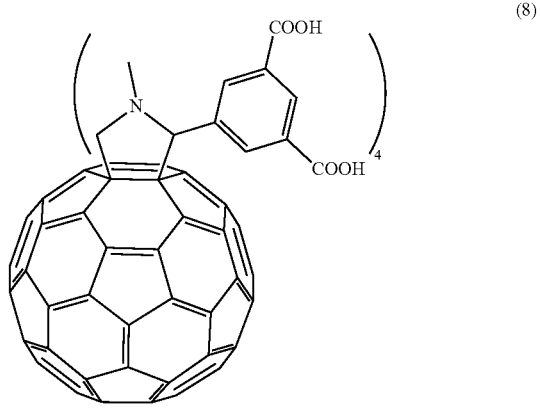

(8)

[Formula 10]

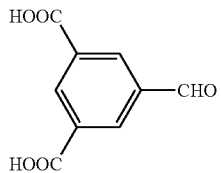

(9)

[Bronsted Base]

The Bronsted base of the present embodiment includes, for example, an amine having n perfluoroalkyl chain.

The amine having the perfluoroalkyl chain can be obtained, for example, by tosylating the hydroxyl group of the alcohol having the perfluoroalkyl chain, then phthalimidizing the resulting tosyl group, and further aminating the resulting imide group.

Specific structures are, for example, Compound 10 represented by the following formula (10) and Compound 11 represented by the formula (11).

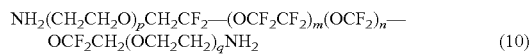

In the formula, p and q are 1 to 3; m is 1 to 30; and n is 0 to 30.

When p and q are 0, the pKb of the amino group is low, which is not preferable. In addition, when p and q are 4 or more, the molecular weight increases, which is not preferable.

$$CF_3CF_2CF_2CF_2-(OCF_2CF_2)_2-OCF_2CH_2OCH_2CH_2NH_2 \quad (11)$$

[Specific Examples of Fullerene Compounds]

Examples of the fullerene compound according to the present embodiment are described below, but the present invention is not limited to these compounds.

Specific examples of the fullerene compound represented by the general formula (1) according to the present embodiment are shown in table 1.

TABLE 1

| | X | $R_1$ | $R_2$ | $R_3$ | $n_1$ | $n_2$ | $m_1$ | $m_2$ |
|---|---|---|---|---|---|---|---|---|
| Compound A |  (phenyl-C60-butyric acid carboxylate, ×2) | $-(CH_2CH_2O)_pCH_2CF_2-(OCF_2CF_2)_m(OCF_2)_n-OCF_2CH_2(OCH_2CH_2)_q-$<br>$p = q = 1$<br>$m = n = 10$ | H | H | 2 | 1 | 2 | 1 |
| Compound B | (phenyl-C60-butyric acid carboxylate, ×2) | $CF_3CF_2CF_2CF_2-(OCF_2CF_2)_2-OCF_2CH_2OCH_2CH_2-$ | H | H | 2 | 1 | 2 | 1 |
| Compound C | (N-methyl pyrrolidino-C60 with bis-carboxylate aryl, ×4) | $-(CH_2CH_2O)_pCH_2CF_2-(OCF_2CF_2)_m(OCF_2)_n-OCF_2CH_2(OCH_2CH_2)_q-$<br>$p = q = 1$<br>$m = n = 10$ | H | H | 8 | 1 | 2 | 4 |
| Compound D | (N-methyl pyrrolidino-C60 with bis-carboxylate aryl, ×4) | $CF_3CF_2CF_2CF_2-(OCF_2CF_2)_2-OCF_2CH_2OCH_2CH_2-$ | H | H | 8 | 1 | 1 | 8 |
| Compound G | $C_n(OH)_{x-y}(OSO_3^\ominus)_y$<br>$C_n = C_{60}$,<br>$x = 10, y = 5$ | $CF_3CF_2CF_2CF_2-(OCF_2CF_2)_2-OCF_2CH_2OCH_2CH_2-$ | H | H | 5 | 1 | 1 | 5 |

Compound A represented by formula (A) is an ionic liquid formed from Compound 7 and Compound 10.

In the formula (A), p and q are 1 and m and n are 10.

[Formula 11]

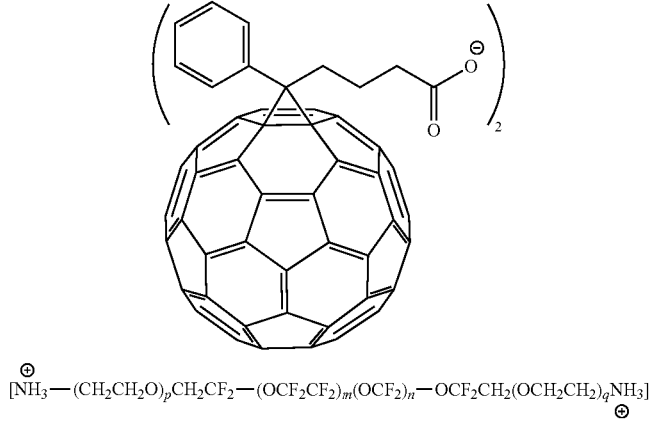

(A)

Compound B represented by formula (B) is an ionic liquid formed from Compound 7 and Compound 11.

[Formula 12]

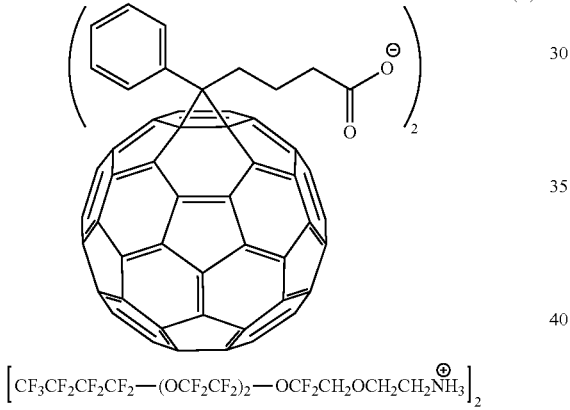

(B)

Compound C represented by formula (C) is an ionic liquid formed from Compound 8 and Compound 10.

In formula (C), p and q are 1, and m and n are 10.

[Formula 13]

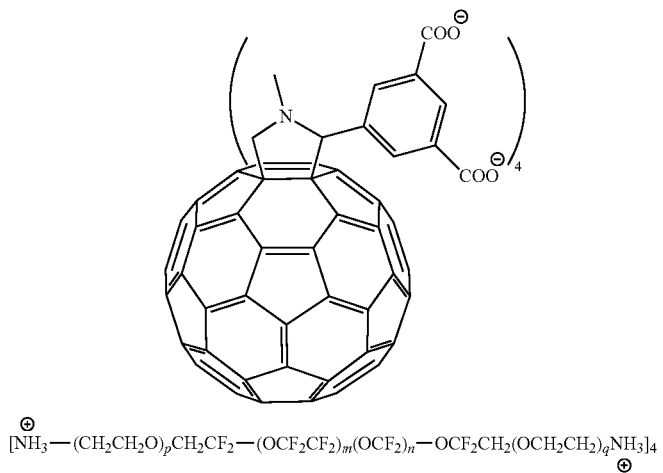

(C)

Compound D represented by formula (D) is an ionic liquid formed from Compound 8 and Compound 11.

[Formula 14]

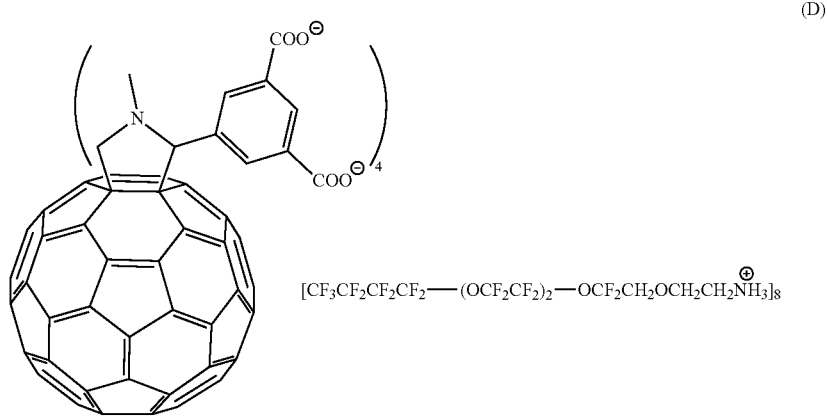

(D)

Compound G represented by formula (G) is an ionic liquid formed from Compound 6A and Compound 11.
In the formula, x is 10 and y is 5.

[Formula 15]

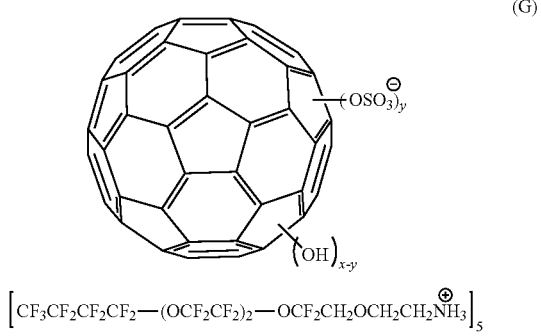

(G)

(Method for Synthesizing Fullerene Compound (Ionic Liquid))

Next, a method for synthesizing the ionic liquid according to the present embodiment will be described. The ionic liquid is synthesized from a B roasted acid and a Bronsted base. For example, a carboxylic acid having a fullerene skeleton and an amine having a perfluoropolyether as a main skeleton arc mixed in an equivalent amount and neutralized.

(Effect of Ionic Liquid)

Generally, since fullerene compounds are less likely to dissolve in organic solvents, it is not easy to introduce perfluoropolyether chains into the fullerene skeleton. According to the method of the present invention, for example, by synthesizing an ionic liquid from a fullerene having a carboxyl group, and a perfluoropolyether chain having an amino group, which both are easily synthesized, the perfluoropolyether chain can be relatively easily introduced into the fullerene skeleton.

(Lubricant)

The lubricant of the present invention is characterized by containing the aforementioned ionic liquid. In the lubricant according to one embodiment of the present invention, the aforementioned ionic liquid may be used alone or in combination with a known lubricant. For example, in the lubricant according to one embodiment of the present invention, long-chain carboxylic acids, long chain carboxylic acid esters, perfluoroalkylcarboxylic acid esters, carboxylic acid perfluoroalkyl esters. perfluoroalkylcarboxylic acid perfluoroalkyl esters, perfluoropolyether derivatives, and the like may be used in combination.

In order to maintain the lubrication effect under severe conditions, an extreme-pressure agent may be used in combination at a compounding ratio of about 30:70 to 70:30 by weight. When metal contact occurs partially in the boundary lubrication region, the extreme-pressure agent reacts with the metal surface by the frictional heat generated by the metal contact, and a film made of the reaction product is formed, thereby performing friction-preventing and wear-preventing action. As the extreme-pressure agent, any of a phosphorus-based extreme-pressure agent, a sulfur-based extreme-pressure agent, a halogen-based extreme-pressure agent, an organometal-based extreme-pressure agent, a composite extreme-pressure agent, and the like can be used.

If necessary, a rust preventing agent may be used in combination. As the rust preventing agent, it is sufficient as long as it can be used as a rust preventing agent for this kind of magnetic recording medium, and examples thereof include phenols, naphthols, quinones, heterocyclic compounds containing nitrogen atoms, heterocyclic compounds containing oxygen atoms, and heterocyclic compounds containing sulfur atoms, in addition, the rust preventing agent may he used as a lubricant by mixing live rust preventing agent with the lubricant, or may be used by laminating two or more layers such that a magnetic layer is formed on the nonmagnetic support, a rust preventing agent layer is applied on the magnetic layer, and then a lubricant layer is applied.

As the solvent of (lie lubricant, an alcohol-based solvent such as isopropyl alcohol (IPA) or ethanol: or a fluorine-based solvent can be used alone or in combination.

Although the molecular weight of the lubricant according to the present invention is not particularly limited, the number average molecular weight (Mn) is preferably in the range of 500 to 20,000, and more preferably in the range of 1,000 to 10,000. This is because it has restorability due to an appropriate viscosity, exhibits suitable lubricant performance, and also has excellent heat resistance.

It is preferable that a molecular weight dispersion (ratio of weight average molecular weight (Mw)/number average molecular weight (Mn)) is controlled to 1.3 or less by molecular-weight-fractionating the lubricant according to the present invention by an appropriate method.

In the present invention, there is no need to set any particular restrictions on the method of molecular weight fractionation, but, for example, a molecular weight fractionation by silica gel column chromatography or gel permeation chromatography (GPC), a molecular weight fractionation by supercritical extraction, or the like can be used.

(Lubricant Layer)

When the lubricant layer is formed by using the lubricant according to the present invention, the lubricant layer can he formed by applying the lubricant by, for example, a dip method using a solution in which the lubricant is dispersed or dissolved in a suitable solvent. The solvent depends on the structure of the ionic liquid, but, for example, a fluorine-based solvent (product name: Vertrel (registered trademark) XF, produced by Mitsui DuPont Fluorochemicals Co., Ltd.) can be preferably used. The method of forming the lubricant layer is not limited to the dip method, and may be a film formation method such as a spin coating method, a spray method, a paper coating method, or the like.

In the present invention, it is preferable to perform heat treatment on the magnetic recording medium after the lubricant layer is formed. By performing this heat treatment, the bonding between the lubricant layer and the protective layer can be improved and the adhesion can be improved, which is suitable for the present invention. The heat treatment temperature is preferably 80 to 180° C. If the temperature is lower than 80° C., the adhesion is not sufficient, and on the other hand, if the temperature is higher than 180° C. the lubricant may be thermally decomposed, which is not preferable. The heat treatment time is preferably 5 to 120 minutes. In the prevent invention, the magnetic recording medium may be subjected to UV irradiation treatment before or after the heat treatment in order to further improve the adhesion of the formed lubricant layer to the protective layer.

In the present invention, the thickness of the lubricant layer is preferably 5 to 25 Å. If the thickness is less than 5 Å, the lubricant performance as the lubricant layer may be deteriorated. A thickness exceeding 25 Å is not preferable from the viewpoint of thinning the film.

(Protective Layer)

A carbon based protective layer may be preferably used as the protective layer in the present invention. In particular, an amorphous carbon protective layer is preferable. The protective layer is particularly preferably a carbon-based protective layer because the interaction between fullerenes of the lubricant of the present invention and the protective layer is further enhanced, and the effect of the present invention is further exerted. In order to adjust the adhesion between the carbon-based protective layer and the lubricant layer, the content of hydrogen and/or nitrogen can be adjusted by using a carbon-based protective layer of hydrogenated-carbon and/or nitrogenated-carbon. In this case, the content of hydrogen is preferably 3 to 20 atom % as measured by the hydrogen forward scattering method (HFS). The content of nitrogen is preferably 4 to 15 atom % as measured by X-ray photoelectron spectroscopy (XPS).

In the carbon-based protective layer of the present invention, if is not necessary that hydrogen and/or nitrogen is uniformly contained in the entire protective layer, and in particular, it is preferable to use a compositionally graded layer in which nitrogen is contained on the lubricant layer side of the protective layer and hydrogen is contained on the magnetic layer side.

When the carbon-based protective layer is used in the present invention, the film can be formed by. for example, a DC magnetron sputtering method. The amorphous carbon protective layer is preferably formed by a plasma CVD method. By forming the film by the plasma CVD method, the surface of the protective layer becomes uniform and the film is formed densely. Therefore, it is preferable to form the lubricant layer according to the present invention on the protective layer formed by the CVD method having a smaller roughness.

In the present invention, the thickness of the protective layer is preferably 10 to 70 Å. If it is less than 10 Å, the performance as a protective layer may be degraded. A thickness exceeding 70 Å is not preferable from the viewpoint of thinning the film.

(Magnetic Recording Medium)

In the magnetic recording medium of the present invention, the substrate is preferably a glass substrate or an aluminum substrate. Since the glass subsume has rigidity and excellent smoothness, it is suitable for high recording density. As the glass substrate, for example, an aluminosilicate glass substrate may be used, and especially, a chemically strengthened aluminosilicate glass substrate is suitable.

In the present invention, it is preferable that the roughness of the main surface of the substrate is ultra-smooth with $R_{max}$ of 6 nm or less and $R_a$ of 0.6 nm or less. Here, the surface roughness $R_{max}$ and $R_a$ are based on live standards of JIS B 0601.

The magnetic recording medium of the present invention includes at least a magnetic layer, a protective layer, and a lubricant layer containing the lubricant according to the present invention on a substrate. In the present invention, the magnetic layer is not particularly limited and may be a magnetic layer for in-plane recording or a magnetic layer for perpendicular recording.

In the magnetic recording medium of the present invention, a base layer may be provided between the substrate and the magnetic layer as necessary. Further, an adhesion layer, a soft magnetic layer, or the like may be provided between the base layer and the substrate. In this case, the base layer may be, for example, a Cr layer; a Ta layer; a Ru layer; or an alloy layer of CrMo, CoW, CrW, CrV, CrTi, or the like. And as the adhesion layer, for example, an alloy layer of CrTi, NiAl, AlRu, or the like may be used. The soft magnetic layer may be. for example, a CoZrTa alloy film.

The magnetic recording medium of the present invention is particularly suitable as a magnetic recording medium to be mounted on a LUL (Load Unload) type magnetic recording medium device. The magnetic recording medium of the present invention having high reliability under a low flying height is suitable because stable operation of the magnetic recording medium is required even under a low flying height of 10 nm or less, due to lowering of the flying height of the magnetic head caused by introduction of the LUL method.

Second Embodiment

In the second embodiment, only a portion related to a configuration different from that of the first embodiment will be mainly described.

[Fullerene Compound]

The fullerene compound according to the second embodiment of the present invention is an ionic liquid represented by the general formula (1), wherein the ionic liquid is formed from Bronsted acid ($H_{n1}X$) and Bronsted base ($[(R_2R_3)N—]_{m1}—R_1$); and the Bronsted acid ($H_{n1}X$) contains a perfluoroalkyl chain and the Bronsted base ($R_2$—N($R_3$)—$R_1$) contains a fullerene-containing group.

[Formula 16]

$$(X^{n1-})_{n_2} \left( \left[ HN^+ \begin{array}{c} R_2 \\ | \\ | \\ R_3 \end{array} \right]_{m_1} R_1 \right)_{m_2} \quad (1)$$

In the general formula (1), at least one of $R_1$, $R_2$, and $R_3$ is a hydrocarbon group having 1 to 20 carbon atoms; X has a perfluoroalkyl chain; and at least one of $R_1$, $R_2$, and $R_3$ has a fullerene skeleton. $R_2$ and $R_3$ may be bonded to each other to form a nitrogen containing heterocycle. $n_1$, $n_2$, $m_1$, and $m_2$ are integers of 1 to 6, and $n_1 \times n_2 = m_1 \times m_2$.

The fullerene skeleton is preferably $C_{60}$ or $C_{70}$.

Preferably, $n_1$ is 1 or 2, $n_2$ is 1 to 6, and $n_1 \times n_2 = m_1 \times m_2$. More preferably, $n_1$ is 1 or 2, $n_2$ is 1 to 4, and $n_1 \times n_2 = m_1 \times m_2$.

Preferably, $m_1$ is an integer of 2 to 6 and $m_2$ is 1. More preferably, $m_1$ is an integer of 2 to 4 and $m_2$ is 1. When $m_1$ is 2 or more, both lubrication and heat resistance can be achieved.

If $m_1$ is an integer of 2 to 6, then $R_1$ is a hydrocarbon group with $m_1$ bonding sites. The hydrocarbon group may have a substituent. The hydrocarbon group preferably has a fullerene skeleton.

[Bronsted Acid]

The Bronsted acids of the present embodiment include, for example, a sulfonic acid having a perfluoroalkyl chain, a carboxylic acid having a perfluoroalkyl chain, and the like.

The sulfonic acid having a perfluoroalkyl chain has, for example, a sulfonic acid group (—$SO_3H$) at the terminal of a compound having the skeleton of structural formulas (2) to (5). In this case, the sulfonic acid having a perfluoroalkyl chain can be synthesized, for example, by the method described in JP 2016-9509 A, by using Fomblin (registered trademark) Z-DOL (Structural formula: $HOCH_2CF_2$ $(OCF_2CF_2)_m(OCF_2)_n$ —$OCF_2$—$CH_2OH$ or $CF_3CF_2CF_2CF_2$—$(OCF_2CF_2)_2$—$OCF_2CH_2OH$) or the like, manufactured by Solvay Solexis, as a raw material.

The specific structure id, for example, Compound 12 represented by formula (12) or Compound 13 represented by formula (13), but is not limited thereto.

$$HO_3S(CH_2)_3OCH_2CF_2—(OCF_2CF_2)_m(OCF_2)_n— \\ OCF_2CH_2O(CH_2)_eSO_3H \quad (12)$$

In the formula, m is 1 to 30 and n is 0 to 30.

$$CF_3CF_2CF_2CF_2—(OCF_2CF_2)_2—OCF_2CH_2O(CH_2)_3 \\ SO_3H \quad (13)$$

The carboxylic acid having a perfluoroalkyl chain has a carboxylic acid group at the end of a perfluoroalkyl chain having 1 to 20 carbon atoms, and examples thereof include undecafluorohexanoic acid, heptadecafluorononanoic acid, tricosafluorododecanoic acid, and the like. Further, the compound is synthesized by using Fomblin Z-DOL (Structural formula: $HOCH_2CF_2(OCF_2CF_2)_m(OCF_2)_n$—$OCF_2$—$CH_2OH$ or $CF_3CF_2CF_2CF_2$—$(OCF_2CF_2)_2$—$OCF_2CH_2OH$) or the like manufactured by Solvay Solexis as a raw material.

The carboxylic acid having the perfluoroalkyl chain may he commercially available. Commercial products include, for example. Fomblin Z-DIAC (number average molecular weight, about 2,000) (formula 14), Fomblin Z-DIAC 4000 (number average molecular weight, about 4,000), Fluorolink (registered trademark) C 10 (number average molecular weight, about 1,700), perfluoro-3,6,9-trioxadecanoic acid (formula 15), and the like, which all are manufactured by Solvay Solexis.

The specific structure is for example, Compound 14 represented by formula (14) or Compound 15 represented by formula (15), but is not limited thereto.

$$HOOCCF_2\text{·}(OCF_2CF_2)_m(OCF_2)_n—OCF_2COOH \quad (14)$$

In the formula, m is 1 to 30 and n is 0 to 30.

$$CF_3CF_2CF_2CF_2—(OCF_2CF_2)_2—OCF_2COOH \quad (15)$$

In the present embodiment, the carboxylic acid having a perfluoroalkyl chain or sulfonic acid having a perfluoroalkyl chain preferably hits a skeleton of structural formula (3) among the skeletons of structural formulas (2) to (4). The structure formula (3) has the same main skeleton as the compounds which exhibit excellent lubricity such as Fomblin Z-DOL (Structural formula: $HOCH_2CF_2$—$(OCF_2CF_2)_m(OCF_2)_n$—$OCF_2CH_2OH$) and Fomblin Z-DIAC (Structural formula: $HOOCCF_2$—$(OCF_2CF_2)_m(OCF_2)_n$—$OCF_2COOH$), which are manufactured by Solvay Solexis.

[Breasted Base]

The Bronsted base of the present embodiment includes, for example, an amine having a fullerene skeleton.

As the amine having the fullerene skeleton, for example. J 204 (Compound 16) represented by formula (16), which is manufactured by Frontier Carbon Corporation, is preferably used.

[Formula 17]

(16)

[Specific Examples of Fullerene Compounds]

Examples of the fullerene compounds according to the present embodiment are described below, but the present invention is not limited to these compounds.

Specific examples of the fullerene compound represented by the general formula (1) according to the present embodiment are shown in Table 2.

TABLE 2
| | X | $[(R_2R_3)HN^{\oplus}]_{m1}$—$R_1$ |
|---|---|---|
| Compound E | $CF_3CF_2CF_2CF_2$—$(OCF_2CF_2)_2$—$OCF_2CH_2O(CH_2)_3SO_3^-$ | 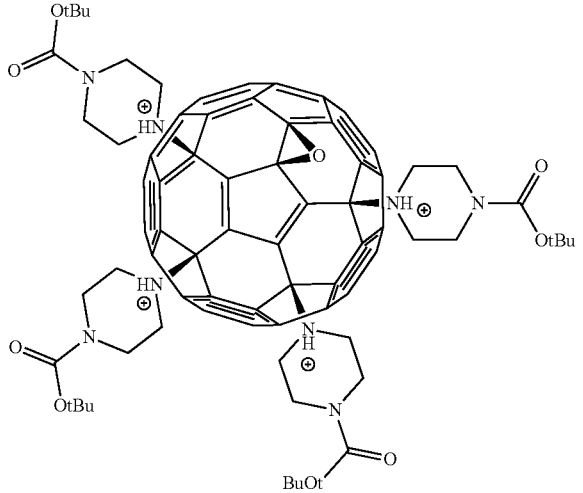 |
| Compound F | $CF_3CF_2CF_2CF_2$  $(OCF_2CF_2)_2$—$OCF_2COO^-$ | 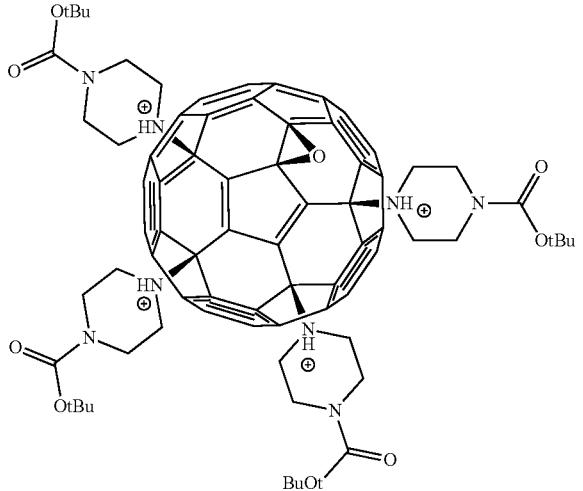 |
| | $R_2$ | $R_3$ | $n_1$ | $n_2$ | $m_1$ | $m_2$ |
|---|---|---|---|---|---|---|
| Compound E | | 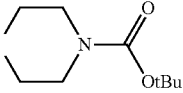 | 1 | 4 | 4 | 1 |
| Compound F | | 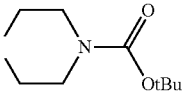 | 1 | 4 | 4 | 1 |

Compound E represented by formula (E) is an ionic liquid formed from Compound 16 and Compound 13.

[Formula 18]

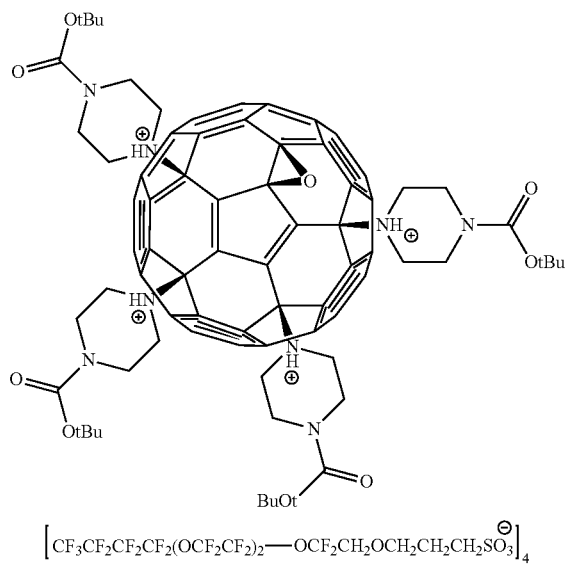

(E)

Compound F represented by formula (F) is an ionic liquid formed from Compound 16 and Compound 15.

[Formula 19]

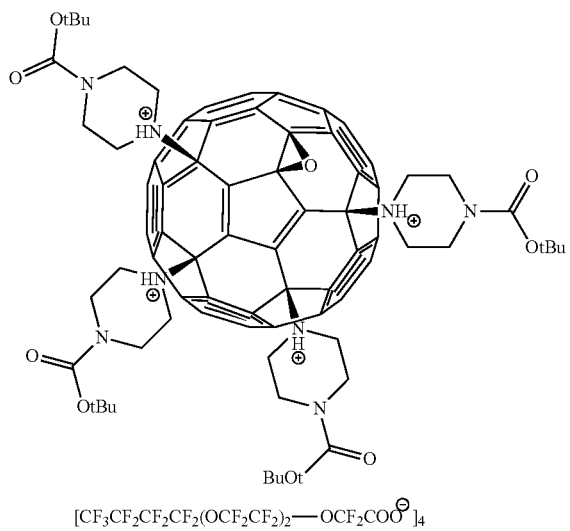

(F)

The thermal decomposition temperature of the ionic liquid is preferably 250° C. or higher, more preferably 300° C. or higher. Even more preferably, the temperature is 350° C. or higher. When the thermal decomposition temperature of the ionic liquid is 250° C. or higher, lubricity can be maintained even when heating is performed, for example, during recording by the HAMR system.

EXAMPLES

Hereinafter, the present invention will be specifically described on the basis of examples. The present invention is not limited to these examples.

Synthesis Example 1

<Synthesis of Compound 6A>

Compound 6A represented by the following formula (6A) was synthesized as the Bronsted acid of the present invention by the method described in JP 2005-8564A using $C_{60}$ made by Frontier Carbon Corporation as a raw material.

[Formula 20]

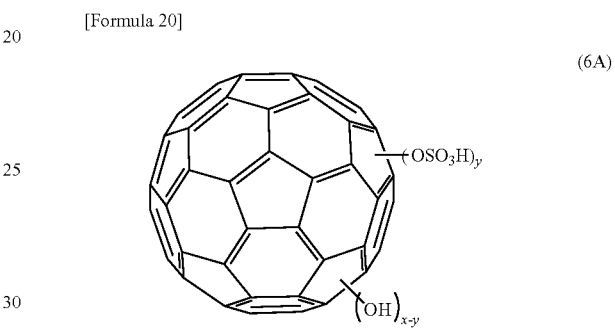

(6A)

In the formula, x is 10 and y is 5.

The elemental analysis results of the obtained Compound 6A were shown as follows:

C: 55.74%; H: 0.78%; S: 12.52%.

Synthesis Example 2

<Synthesis of Compound 11>

Compound 11 as the Bronsted base of the present invention was synthesized by reacting 1H, 1H-Perfluoro-3,6,9-trioxatridecan-1-ol (structure formula: $CF_3CF_2CF_2CF_2$—$OCF_2CF_2$—$OCF_2CH_2OH$, number average molecular weight: 548) manufactured by Alfa Chemistry with 2-(2-chloroethoxy)tetrahydro-2H-pyran, tosylating the hydroxyl group of the deprotected compound, phthalimidizing the resulting tosyl group, and then aminating the resulting imide group.

(11)

Synthesis Example 3

<Synthesis of Compound 7>

Compound 7 as the Bronsted acid of the present invention was synthesized as a hydrolysate of bis-phenyl $C_{61}$ butyric acid methyl (Frontier Carbon Corporation).

[Formula 21]

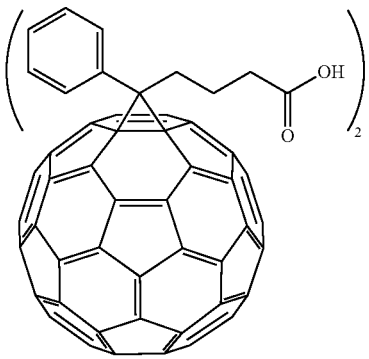

Synthesis Example 4

<Synthesis of Compound 8>

Compound 8 as the Breasted acid of the present invention was synthesized as a hydrolysate of a compound obtained by reacting fullerene $C_{60}$ (Frontier Carbon Corporation) with N-methylglycine and an aldehyde obtained from the partial reduction of trimethyl benzene-tricarboxylate.

[Formula 22]

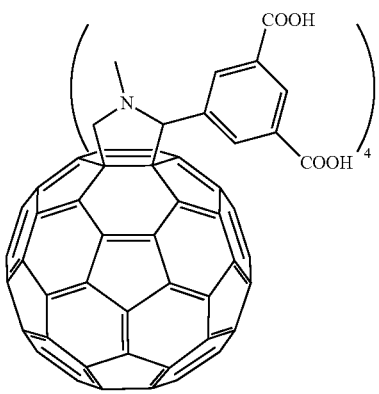

Example 1

[Production of Fullerene Compound]

1.07 g (Mw 1072, 1.0 mmol) of Compound 7 as the Bronsted acid of the present invention and 50 mL of THF were charged into a 100 mL eggplant flask under a nitrogen atmosphere, and were stirred and dissolved at room temperature. 1.77 g (Mw 591, 3.0 mmol) of Compound 11, as the Bronsted base of the present invention, was added to this solution, and after stirring for 1 hour at room temperature and 1 hour at 40° C., the solvent was distilled off. The residue was washed by decantation of heptane, and the supernatant was removed repeatedly until the washings showed pH 7, to synthesize Compound B as the fullerene compound of the first embodiment of the invention.

[Preparation of Lubricant Layer-Forming Solution]

The synthesized Compound B was dissolved in Vertrel XF (product name, made by Mitsui DuPont Fluorochemicals Co., Ltd) to obtain a lubricant layer-forming solution. The concentration of the fullerene compound (lubricant) was 0.27 mass %. The solubility of Compound B in Vertrel XF was 0.36 mass %.

[Manufacture of a Magnetic Recording Medium]

<Formation of Magnetic Layer, Protective Layer, and the Like>

FIG. 1 shows a magnetic recording medium 11 according to Example 1.

The magnetic recording medium 11 was formed by sequentially forming a magnetic layer 2, a protective layer 3, and a lubricant layer 4 on a nonmagnetic substrate 1.

The cleaned glass substrate (manufactured by HOYA, external dimensions 65 mm) was housed in a film formation chamber of a DC magnetron sputtering apparatus (C-3040, manufactured by Anelva Corporation), and the inside of the film formation chamber was evacuated to an ultimate vacuum degree of $1\times10^{-5}$ Pa.

Thereafter, an adhesion layer having a thickness of 10 nm was formed on the glass substrate by sputtering method using a CrTi target. Next, a first soft magnetic layer having a layer thickness of 25 nm was formed at a substrate temperature of 100° C. or less by using a target of Co-20Fe-5Zr-5Ta (Fe content of 20 atom %, Zr content of 5 atom%, Ta content of 5 atom %, and the balance Co) as a soft magnetic base layer on the adhesion layer by a sputtering method, and an intermediate layer made of Ru having a layer thickness of 0.7 nm and a second soft magnetic layer made of Co-20Fe-5Zr-5Ta having a layer thickness of 25 nm were formed thereon.

Next, a seed layer having a layer thickness of 5 nm was formed on the soft magnetic base layer by sputtering method using a Ni-6W {W content of 6 atom %, and the balance Ni} target. Thereafter, as a first orientation control layer, a Ru layer having a thickness of 10 nm was formed on the seed layer by sputtering method at a sputtering pressure of 0.8 Pa. Next, as a second orientation control layer, a Ru layer having a thickness of 10 run was formed on the first orientation control layer by sputtering method at a sputtering pressure of 1.5 Pa.

Subsequently, a first magnetic layer made of 91 (Co15Cr16Pt)-6($SiO_2$)-3($TiO_2$) {91 mol % of an alloy having Cr content of 15 atom %, Pt content of 16 atom %, and the balance Co; 6 mol % of an oxide made from $SiO_2$; and 3 mol % of an oxide made from $TiO_2$} was formal on die second orientation control layer by sputtering method at a sputtering pressure of 2 Pa and a layer thickness of 9 nm.

Next, a nonmagnetic layer of 88 (Co30Cr)-12($TiO_2$) {88 mol % of an alloy having Cr content of 30 atom % and the balance Co, and 12 mol % of an oxide made from $TiO_2$} was formed on the first magnetic layer with a layer thickness of 0.3 nm by sputtering method. Thereafter, a second magnetic layer made of 92 (Co11Cr18Pt)-5($SiO_2$)-3($TiO_2$) {92 mol % of an alloy having Cr content of 11 atom %, Pt content of 18 atom %, and the balance Co; 5 mol % of an oxide made from $SiO_2$; and 3 mol % of an oxide made from $TiO_2$} was formed on the nonmagnetic layer by sputtering method at a sputtering pressure of 2 Pa and a layer thickness of 6 nm.

Thereafter, a nonmagnetic layer made of Ru was formed on the second magnetic layer with a thickness of 0.3 nm by sputtering method. Next, the third magnetic layer was formed on the nonmagnetic layer with a layer thickness of 7 nm by sputtering method using a target made of Co-20Cr-14Pt-3B {Cr content of 20 atom %, Pt content of 14 atom %. B content of 3 atom %, and the balance Co} at a sputtering pressure of 0.6 Pa. Next, a protective layer made of carbon and hydrogen, which has a thickness of 20 nm, was formed by CVD method. The hydrogen contained in the protective layer was about 15 atom %.

<Formation of the Lubricant Layer>

Lubricant was applied onto the protective layer using a dip method. That is, after the prepared lubricant layer-forming solution was placed in the dipping tank of the dip coating apparatus, the substrate in which the layers up to the protective layer were formed was immersed in the lubricant layer-forming solution, and then the substrate was pulled up from the dipping tank at a constant speed to apply the lubricant layer-forming solution to the surface of the protective layer of the substrate. The thickness of five lubricant layer was 1.4 nm.

Example 2

In a 100 mL eggplant flask under a nitrogen atmosphere, 1.57 g (Mw 1568, 1.0 mmol) of Compound 8 as the Bronsted acid of the present invention and 50 mL of THF were charged and stirred at room temperature to dissolve. 7.09 g (Mw 591. 12.0 mmol) of Compound 11, as the Bronsted base of the present invention, was added to this solution, and after stirring at room temperature for 1 hour and at 40° C. for 1 hour, the solvent was distilled off. The residue was washed by decantation of heptane and the supernatant was removed repeatedly until the washings showed pH 7, to synthesize Compound D as the fullerene compound of the first embodiment of the invention.

A lubricant layer was formed and a magnetic recording medium was manufactured in the same manner as in Example 1 except that Compound D was used.

Example 3

In a 100 mL eggplant flask under a nitrogen atmosphere, 1.25 g (Mw 1251, 1.0 mmol) of Compound 16 (J 204 of Frontier Carbon Corporation) as the Bronsted base of the present invention and 50 mL of THF were charged and stirred at room temperature to dissolve, 3.37 g (Mw 562, 6.0 mmol) of Compound 15, as the Bronsted acid of the present invention, was added to this solution, and stirred at room temperature for 1 hour and at 40° C. for 1 hour, and then the solvent was distilled off. The residue was washed by decantation of heptane, and the supernatant was removed repeatedly until the washings showed pH 7, to synthesize Compound F as the fullerene compound of the second embodiment of the invention.

A lubricant layer was formed and a magnetic recording medium was manufactured in the same manner as in Example 1 except that Compound F was used.

Example 4

1.29 g (Mw 1291, 1.0 mmol) of Compound 6A as the Bronsted acid of the present invention, 50 mL of THF and 50 mL of water were charged into a 100 mL eggplant flask under a nitrogen atmosphere, and the mixture was stirred and suspended at room temperature, 7.09 g (Mw 591, 12.0 mmol) of Compound 11, as the Bronsted base of the present invention, was added to this solution, stirred at room temperature for 12 hours and at 40° C. for 10 hours, and then the solvent was distilled off. The residue was washed by decantation of heptane and the supernatant was removed repeatedly until the washings showed pH 7, to synthesize Compound G as the fullerene compound of the first embodiment of the invention.

A lubricant layer was formed and a magnetic recording medium was manufactured in the same manner as in Example 1 except that Compound G was used.

Comparative Example 1

Compound H, which was an ionic liquid of Z-DIAC (Molecular weight 2,000) and octadecylamine, was obtained.

A lubricant layer was formed and a magnetic recording medium was manufactured in the same manner us in Example 1 except that Compound H was used.

Comparative Example 2

Compound I, which was an ionic liquid of Z-DIAC (Molecular weight 2,000) and 1H, 1H, 2H, 2H-perfluorodecylamine, was obtained.

A lubricant layer was formed and a magnetic recording medium was manufactured in the same manner as in Example 1 except that Compound I was used.

(Evaluation of Fullerene Compounds and Lubricant Layers)

Compound B, Compound D, Compound E, and Compound G of Examples 1 to 4; Compound H and Compound I of Comparative Examples 1 and 2; and the lubricant layers containing these compounds were evaluated by the evaluation methods described later. The evaluation results are shown in Table 3.

[Measurement of Thermal Decomposition Temperature of Fullerene Compounds]

With TG-DTA (Manufacturer: Seiko Instruments, Model: EXSTAR 6000), weight loss relative to temperature was measured for fullerene compounds, and the temperature at 5% weight loss was defined as the pyrolysis temperature. As the measurement conditions, a temperature rising rate of 10° C./min and an air flow rate of 200 mL/min were used.

[Measurement of Friction Coefficient of Lubricant Layer]

Samples were prepared by dip coating the lubricant on a slide glass as the substrate. A 0.2% by mass solution of an ionic liquid using Vertrel/ethanol (70/30) as a solvent was prepared as the lubricant. The dip coating was carried out by pulling up the slide glass from the lubricant tank at a speed of 50 mm/min.

Using an automatic friction measurement device (manufacturer: Kyowa Interface Chemical, Model No.: TribosterTS-501), the friction coefficient of the sample was measured under the following conditions: point contact (3 mm Steel Sphere), weight 15 g, speed 1.7 mm/sec, distance 20 mm, and repetition rate 12. The 12th value is show n in Table 3.

TABLE 3

|  |  | Pyrolysis temperature | Coefficient of friction without heat treatment | Coefficient of friction 140° C. for 60 minutes | Coefficient of friction 250° C. for 60 minutes |
|---|---|---|---|---|---|
| Example 1 | Compound B | 330 | 0.13 | 0.17 | 0.20 |
| Example 2 | Compound D | >350 | 0.09 | 0.13 | 0.19 |
| Example 3 | Compound F | 320 | 0.12 | 0.15 | 0.19 |
| Example 4 | Compound G | 330 | 0.11 | 0.15 | 0.19 |
| Comparative Example 1 | Compound H | 200 | 0.14 | 0.24 | 0.36 |
| Comparative Example 2 | Compound I | 190 | 0.12 | 0.15 | 0.39 |

As shown in Table 3, in Examples 1 to 4, the synthesized fullerene compounds have a thermal decomposition temperature of 300° C. or higher and have sufficient heat resistance.

In Examples 1 to 4, not only a low coefficient of friction was obtained without heat treatment, but also a low coefficient of friction was obtained by heat treatment at 140° C. for 60 minutes and 250° C. for 60 minutes. On the other hand, in Comparative Examples 1 to 2, the function coefficient increased due to heating.

As described above, the fullerene compound of the present invention is an ionic liquid formed from a Bronsted acid and a Bronsted base, and one of the Bronsted acid and the Bronsted base contains a group having a fullerene, and the other one of the Bronsted acid and the Bronsted base contains a perfluoroalkyl chain. When the fullerene and the perfluoroalkyl chain are molecularized by ionic bonds, both lubricity and heat resistance can be achieved.

[Description of the Signs]

1 . . . Nonmagnetic Substrate,

2 . . . Magnetic Layer,

3 . . . Protective Layer,

4 . . . Lubricant Layer,

11 . . . Magnetic Recording Medium,

The invention claimed is:

1. A fullerene compound, which is an ionic liquid represented by general formula (1), wherein the ionic liquid is formed from a Bronsted acid $(H_{n_1}X)$ and a Bronsted base $([(R_2R_3)N-]_{m_1}-R_1)$;

one of the Bronsted acid and the Bronsted base comprises a group having a fullerene; and the other one of the Bronsted acid and the Bronsted base comprises a perfluoroalkyl chain,

[Formula 1]

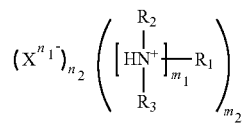

(1)

wherein at least one of $R_1$, $R_2$, and $R_3$ is a hydrocarbon group having 1 to 20 carbon atoms;

at least one of X, $R_1$, $R_2$, and $R_3$ has a fullerene skeleton, and at least one of X, $R_1$, $R_2$, and $R_3$ has a perfluoroalkyl chain;

$R_2$ and $R_3$ may be bonded to each other to form a nitrogen-containing heterocycle; and $n_1$, $n_2$, $m_1$, and $m_2$ are integers of 1 to 6, and $n_1 \times n_2 = m_1 \times m_2$.

2. The fullerene compound according to claim 1, wherein the Bronsted acid, in a molecule, comprises a fullerene skeleton, and a sulfonic acid group or a carboxylic acid group; and the Bronsted base comprises a perfluoropolyether chain.

3. The fullerene compound according to claim 1, wherein the Bronsted acid, in a molecule, comprises a perfluoropolyether chain, and a sulfonic acid group or a carboxylic acid group; and the Bronsted base comprises a fullerene skeleton.

4. The fullerene compound according to claim 1, wherein the Bronsted acid is a compound represented by formula (6), (7), or (8);

the Bronsted base is a compound represented by formula (10) or (11), $$C_n(OH)_{x-y}(OSO_3H)_y \qquad (6)$$

wherein $C_n$ represents a fullerene which is a base structure of polyhydroxylated fullerene hydrogen sulfate ester;

x is a number in the range of 10 to 30;

y is a number in the range of 5 to 10; and $C_n$ is at least one kind selected from $C_{60}$, $C_{70}$, $C_{76}$, $C_{78}$, $C_{80}$, $C_{82}$, and $C_{84}$.

[Formula 2]

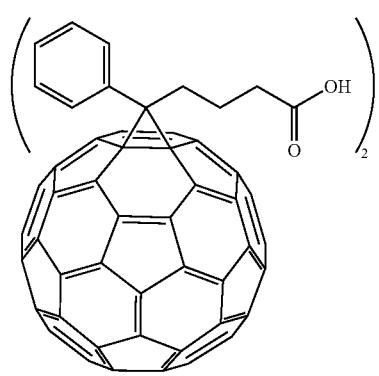

(7)

-continued

[Formula 3]

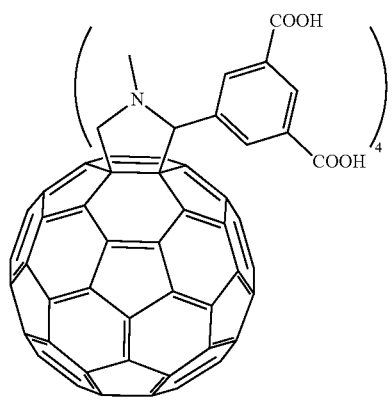
(8)

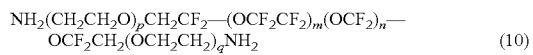
(10)

wherein p and q are 1 to 3; m is 1 to 30; and n is 0 to 30,

(11)

5. The fullerene compound according to claim 1,
wherein the Bronsted acid is a compound represented by any one of the following formulae (12) to (15); and the Bronsted base is a compound represented by formula (16),

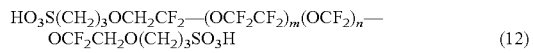
(12)

wherein m is 1 to 30 and n is 0 to 30,

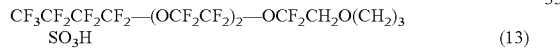
(13)

(14)

wherein m is 1 to 30 and n is 0 to 30, $CF_3CF_2CF_2CF_2$—$(OCF_2CF_2)_2$—$OCF_2COOH$ (15)

[Formula 4]

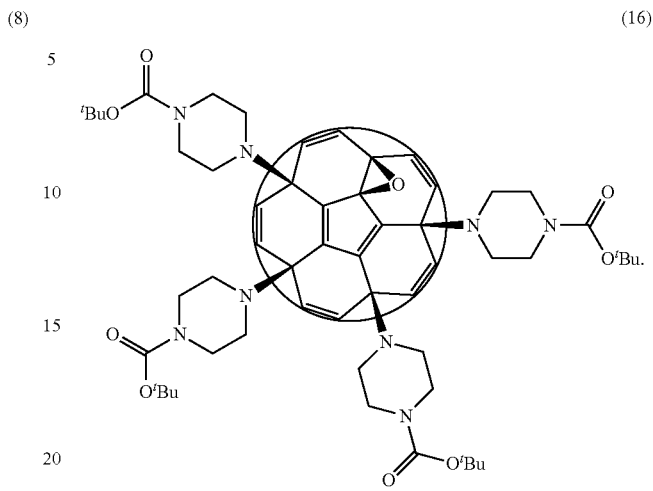
(16)

6. The fullerene compound according to claim 1,
wherein a thermal decomposition temperature of the ionic liquid is 300° C. or higher.

7. The fullerene compound according to claim 1,
wherein a number average molecular weight is in the range of 500 to 20,000.

8. A lubricant for a magnetic recording medium, comprising the fullerene compound according to claim 1.

9. A magnetic recording medium in which at least a magnetic layer, a protective layer, and a lubricant layer are sequentially provided on a substrate,
wherein the lubricant layer contains the fullerene compound according to claim 1.

10. The magnetic recording medium according to claim 9,
wherein the lubricant layer has an average thickness of 0.5 nm to 2.5 nm.

* * * * *